(12) United States Patent
Almannie

(10) Patent No.: US 12,390,178 B1
(45) Date of Patent: Aug. 19, 2025

(54) FLUOROSCOPIC RETROGRADE URETHROGRAM INSTRUMENT

(71) Applicant: KING SAUD UNIVERSITY, Riyadh (SA)

(72) Inventor: Raed Mohammed Abdulla Almannie, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/904,565

(22) Filed: Oct. 2, 2024

(51) Int. Cl.
*A61B 6/00* (2024.01)
*A61B 6/04* (2006.01)
*A61B 6/50* (2024.01)

(52) U.S. Cl.
CPC ............ *A61B 6/481* (2013.01); *A61B 6/0414* (2013.01); *A61B 6/0492* (2013.01); *A61B 6/50* (2013.01)

(58) Field of Classification Search
CPC ..... A61B 6/481; A61B 6/0414; A61B 6/0492; A61B 6/50
See application file for complete search history.

(56) References Cited

U.S. PATENT DOCUMENTS

2015/0238732 A1* 8/2015 Ritmiller ............... A61M 25/01
604/544

OTHER PUBLICATIONS

Knutson (On the Technique of Urethrography, pp. 437-441 2010.*
Anderson, et al.; "Novel treatment for strictures of the distal penile urethra and fossa navicularis", Mayo Clinic, Jun. 13, 2023.

* cited by examiner

*Primary Examiner* — Serkan Akar
(74) *Attorney, Agent, or Firm* — Nath, Goldberg & Meyer; Joshua B. Goldberg

(57) ABSTRACT

Medical manipulation of a patient's penis for examination and treatment of a urethral stricture is performed using a penile clamp assembly with support members for the patient's penis and a slider block, a revolving slide support and a base. The support members include a proximal penile clamp and a distal penile injection support, which support the patient's penis. The slider block has a configuration to allow the penile clamp assembly to slide along a length of the revolving slide support. The revolving slide support uses a hinged mounting arrangement for mounting the revolving slide support on the base.

1 Claim, 4 Drawing Sheets

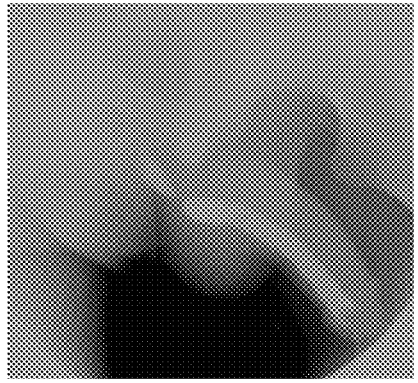
FIG. 3A  FIG. 3B
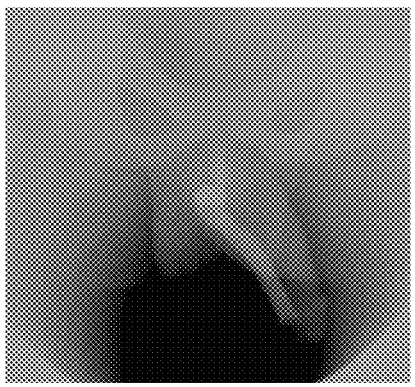
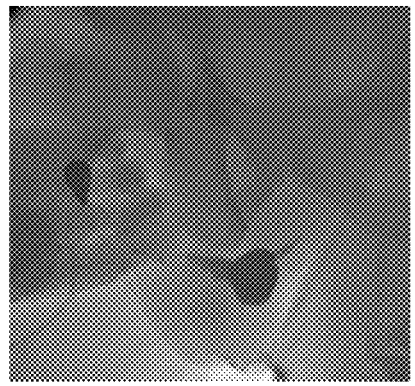
FIG. 3C  FIG. 3D

FLUOROSCOPIC RETROGRADE URETHROGRAM INSTRUMENT

BACKGROUND

Technical Field

The present disclosure relates to retrograde urethrogram (RUG) urethrography procedures, and more particularly to a fluoroscopic retrograde urethrogram instrument for positioning a penis and providing a measurement guide during RUG procedures.

Background Art

Urethral stricture is caused by fibrosis of the corpus spongiosum, leading to narrowing of the urethral lumen. The location could be any part of the urethra where it is surrounded by corpus spongiosum. Urethral strictures are relatively common in men with an associated prevalence of 229 to 627 per 100,000 males. The etiology includes, but is not limited to: idiopathic, iatrogenic, inflammatory and traumatic causation. The most common of those are iatrogenic and idiopathic causes but geographic differences do exist. In general, narrowing of the urethral lumen may lead to significant impact on physical, social and psychological well-being of a patient.

Treatment planning of a urethral stricture depends on its characteristics. In standard medical practice, initial endoscopic treatment can be offered if the stricture is single, short, not obliterated and located in the bulbar region. If reconstructive surgery is planned, the type of surgery also is based on urethral stricture characteristics. It has been found that intraoperative ultrasound changed the type of surgery in 19% of patients and impacted decision making in 26% of patients, due to intraoperative changes in length measurement of the urethral stricture. Once urethral stricture is diagnosed it is important to determine the characteristics of the stricture including: location, length, degree of narrowing and associated anomalies.

Multiple diagnostic tests are available to diagnose and stage urethral stricture, including: retrograde urethrogram (RUG), cystoscopy, ultrasound, MRI and computer tomography. Cystoscopy is commonly used and considered the most specific test, but it is limited by the inability to assess the proximal extent of the stricture. Sonourethrography offers the advantage of assessing the degree of spongiofibrosis and greater accuracy in measuring length. Sonourethrography has some drawbacks including: its operator dependency, decreased accuracy in posterior urethral strictures, and often requires local or general anesthesia. Only 8% of the reported studies used sonourethrography as a diagnostic tool to monitor for stricture recurrence. Cross sectional studies (MRI and CT), have some applications in pelvic fracture related urethral injuries but limited utility in urethral stricture disease.

Currently, retrograde urethrogram urethrography (RUG) is the most commonly used diagnostic tool for urethral strictures and considered the best available test. RUG has been used for over 100 years, but measures to enhance this diagnostic test and overcome its limitations are limited, as described in Table 1:

TABLE 1

| Limitations of retrograde urethrogram (RUG) | |
|---|---|
| Limitation | Effect |
| Oblique position | Underestimation of length |
| Inadequate positioning | Underestimation of length |
| | Increase radiation exposure to patient and technician by trial and error |
| | Cost and time in case the study needed to be repeated |
| Close proximity of technician | Radiation exposure |
| Use of urethral catheter | Can misdiagnose distal urethral strictures if not placed appropriately |
| Different parts of the urethra are at different distances from the X-ray detector (the further the object from the detector the larger it appears) | Penile urethral strictures might will look longer than same length bulbar urethral stricture |
| Different axis of penile and bulbar urethra (bulbar urethra is fixed at pelvic axis while penile urethra depends on the technician) | Discrepancy in the accuracy between penile and bulbar urethral stricture measurements 17 |

In RUG procedures, management options for urethral stricture depend primarily on the length of the stricture. Current radiological assessment tools have limitations in the assessment of the length of urethral strictures. Limitations in RUG procedures include underestimation of length, misdiagnosis, and radiation exposure to patient and medical staff.

It is therefore desired to provide a medical instrument that will overcome the limitations of retrograde urethrograms (RUGs). It is further desired to increase accuracy and safety of RUG by designing an instrument that will increase the performance of this test.

SUMMARY

Medical manipulation of a patient's penis for examination and treatment of a urethral stricture is performed with the aid of a penile clamp assembly comprising support members for the patient's penis and a slider block, a revolving slide support and a base. The support members include a proximal penile clamp and a distal penile injection support, and are attached to the slider block. The slider block is configured to allow the penile clamp assembly to slide along a length of the revolving slide support. The revolving slide support has a hinged mounting arrangement for mounting the revolving slide support on the base. In order to present an observation of correct length indication and avoid errors caused by oblique views and perspective errors, the revolving slide support has imaging ruler markings, suitable for an imaging process used in examination.

BRIEF DESCRIPTION OF THE DRAWINGS

FIGS. 1A and 1B show a configuration of a fluoroscopic retrograde urethrogram instrument. FIG. 1C shows a penile clamp assembly. FIG. 1D shows a revolving arm, and FIG. 1E shows a base.

FIG. 2A shows a side view, in which tube is parallel to the radiology detector plate. FIG. 2B shows an oblique positioning. FIG. 2C shows the oblique positioning similar to that of FIG. 2B, but taken further from the radiology detector plate.

FIGS. 3A-3D are radiographs and an endoscopic image of showing examples of RUG limitations that are addressed by the disclosed technology. FIG. 3A depicts a bulbar urethral stricture, represented by a gap in the radiopaque material. FIG. 3B is an endoscopic image past a dilator showing insertion of a tube assembly. FIG. 3C shows a radiograph in which the intra-operative length visualized from the radiograph was used to estimate a length that translated to a shorter than optimum stint. FIG. 3D shows the examiner hand due to poor control of the imagery.

DETAILED DESCRIPTION

Overview

A fluoroscopic retrograde urethrogram instrument is used for positioning a penis and providing a measurement guide during retrograde urethrogram (RUG) arthrography procedures. The instrument includes a base which is placed under the patient, a radiologically detectable arm rotatably connected to a center of the base and having length indicators thereon, and a slider slidingly mounted on the arm. The arm can be adjusted to the desired angle and locked in place by a locking handle. The position of the slider on the arm can be maintained by a locking clamp, to maintain the patient's penis in a stretched position.

In the present disclosure, "radiological" and "radiologically" refers to the use of medical imaging for visual representation of the function of some organs or tissues. The imaging may be X-ray (roentgenography), ultrasonic, optical and other electromagnetic energy imaging. In a non-limiting example, X-ray imaging is used. During such imaging, radiological markings are often used to identify locations, and to identify measurements corresponding to the imaged tissue.

The instrument has a proximal penile clamp and a distal penile injection support. The distance between the distal penile injection support and the proximal penile clamp allows the edge of a catheter tip syringe to be placed in the fossa navicularis urethrae.

The instrument is intended to address particularly difficulties in RUG procedures.

EXAMPLE

Figure 1A:
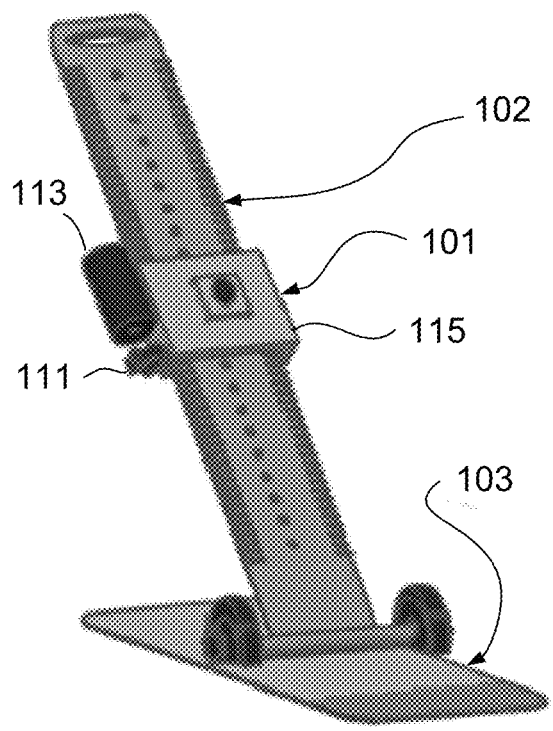
FIGS. 1A-1E are schematic diagrams showing a configuration of apparatus for medical manipulation of a patient's penis for examination and treatment of a urethral stricture.
Figure 1B:
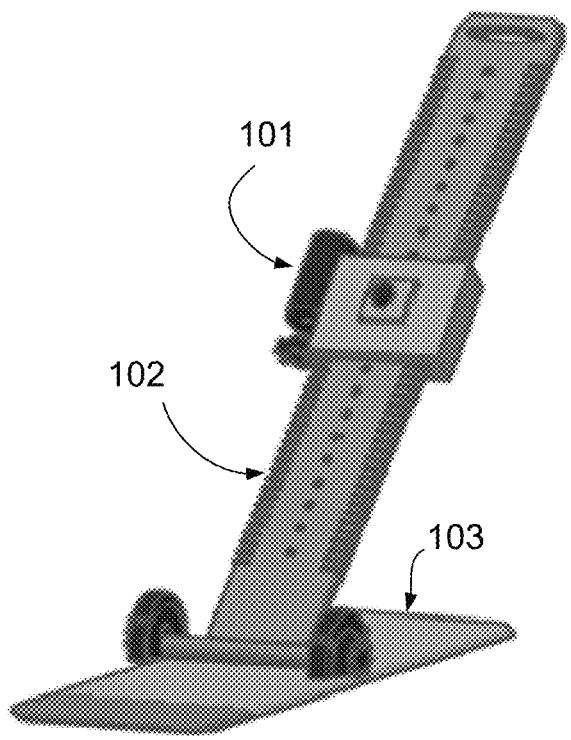
Figure 1C:
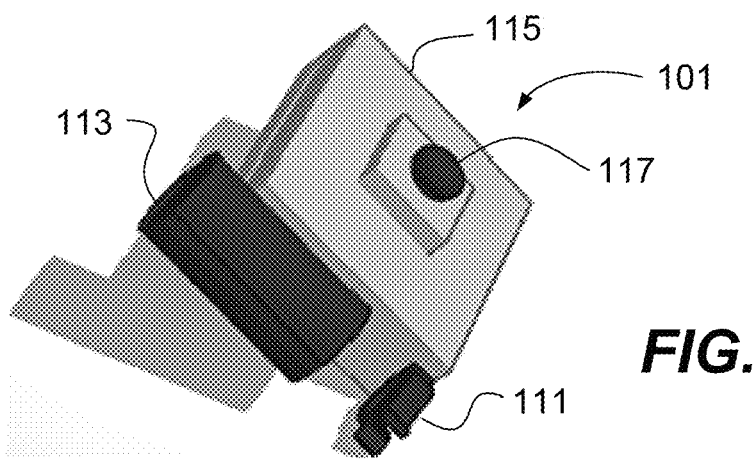
Figure 1D:
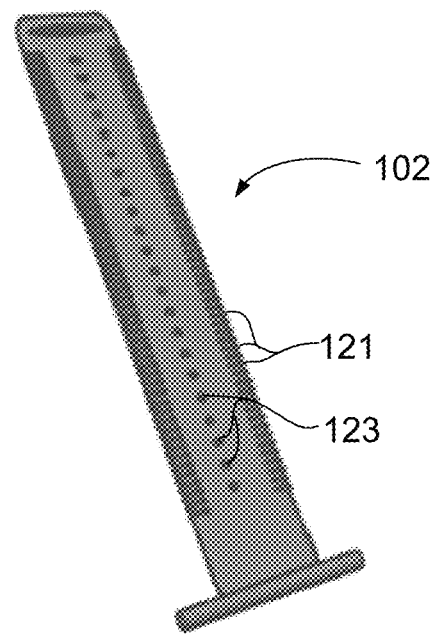
Figure 1E:
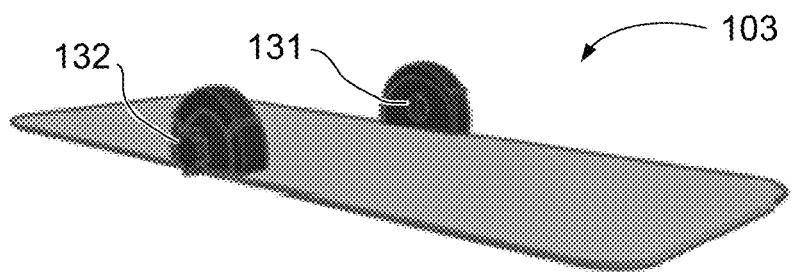

FIGS. 1A and 1B are schematic diagrams showing a configuration of a fluoroscopic retrograde urethrogram instrument, constructed according to the disclosed technique, given as a non-limiting example. FIGS. 1C-1E are schematic diagrams showing components used in the fluoroscopic retrograde urethrogram instrument of FIGS. 1A and 1B. The instrument includes three parts: penile clamp assembly 101, shown in FIG. 1C, revolving arm 102, shown in FIG. 1D, and base 103, shown in FIG. 1E.

Penile clamp assembly 101 includes a penile support arrangement of proximal penile clamp 111 and distal penile injection support 113, and slider block 115. Penile injection support 113, and slider block 115 thus are support members which provide a function of supporting the patient's penis for medical procedures such as examination and/or treatment. The distance between proximal penile clamp 111 and distal penile injection support 113 allows the edge of a catheter tip syringe to be placed in the patient's fossa navicularis. A slider position of slider block 115 along revolving arm 102 can be adjusted by locking mechanism 117, depicted by way of non-limiting example, as a thumbscrew. The adjustment of slider block 115 along revolving arm 102 allows penile clamp assembly 101 to be adjusted in order to provide adequate control of the penis in a stretched position. Revolving arm 102 is provided with a radiological ruler 121, and optionally has lock detents 123, which cooperate with locking mechanism 117.

Radiological ruler markings 121 provide measurement indicia on radiographic images. Alternatively, ruler 121 can provide measurement indicia for other forms of imaging as appropriate for the imaging process used for examination, such as measurement indicia for ultrasonic images.

Base 103 is configured for placement under the patient. Base 103 contains pivot joint 131 with locking handle 132. Pivot joint 131 is shown, by non-limiting example, marked at 45//DEG. Locking handle 131 can fix revolving arm 102 at a desired angle and the angle can be adjusted as desired.

When conducting a RUG study, base 103 is placed under the patient and then the patient is placed in oblique position. Revolving arm 102 is aligned in the same axis as the perineal raphe and the penis. Correct position is confirmed by referring to the marking on the pivot joint 131. After appropriate positioning, revolving arm 102 is fixed in this position by pivot joint 131 and locking handle 132. The slider position of penile camp assembly 101 is moved linearly along revolving arm 102 to reach a desired adequate position and fixed in position by locking mechanism 117. Proximal penile clamp 111 is used to hold the penis in stretched position.

A catheter tip syringe (not shown) filled with contrast is placed through distal penile injection support 113. The radiologist or other medical professional will need one hand to do the injection while maintaining adequate distance during the radiological procedure.

The configuration can be enhanced by providing a remotely controlled injection device, which will significantly reduce radiation exposure to the radiologist.

Figure 2A:
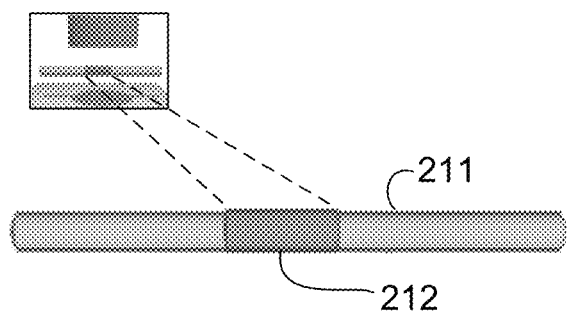
FIGS. 2A-2C are schematic illustrations relating to causes for underestimating the length of a stint insertion tube and stint 212, as radiologically viewed during RUG.
Figure 2B:
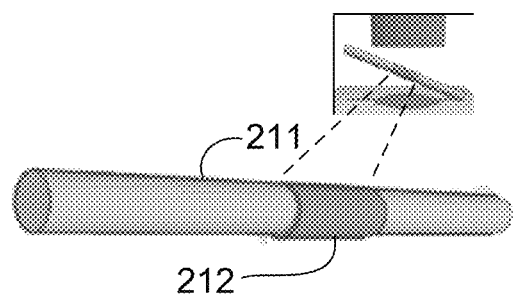
Figure 2C:
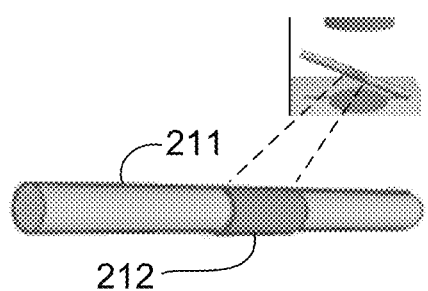

FIGS. 2A-2C are schematic illustrations relating to causes for underestimating the length of a stint insertion tube 211 with stint 212 which may be radiologically viewed during RUG. FIG. 2A shows a side view, in which tube 211 is parallel to the radiology detector plate. Due to the parallel-to-plate position, the length of the stint 212, is easily perceived. FIG. 2B shows an oblique positioning, in which the length of stint 212 has a measurable length which appears to be less than that of stint 212 in FIG. 2A. FIG. 2C shows the oblique positioning similar to that of FIG. 2B, but with tube 211 and stint 212 further from the radiology detector plate, resulting in stint 212 appearing to be shorter. Radiological ruler markings 121 (FIGS. 1A, 1B, 1D) imprint appropriate measurement indicia on the received images, so it is not necessary for the medical professionals to take into account the projection angle of the radiological equipment with respect to the penis or stint.

FIGS. 3A-3D are radiographs and an endoscopic image of showing examples of RUG limitations that are addressed by the disclosed technology. FIG. 3A depicts a bulbar urethral stricture, represented by a gap in the radiopaque material. FIG. 3B is an endoscopic image past a dilator showing insertion of a tube assembly (e.g., tube 211 in FIGS. 2A-2C). FIG. 3C shows a radiograph in which the intra-operative length visualized from the radiograph of FIG. 3A was used to estimate a length that translated to a shorter than optimum stint 212. The result was a longer stricture than anticipated. Hence, inappropriate positioning might lead to underestimation of length and increase radiation in the case the study being repeated. FIG. 3D shows the examiner hand due to poor control of the imagery.

CLOSING STATEMENT

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. Apparatus for medical manipulation of a patient's penis for examination and treatment of a urethral stricture via fluoroscopic imaging, the apparatus comprising:
   a slider block;
   a proximal penile clamp;
   a distal penile injection support, wherein the proximal penile clamp and distal penile injection support are mounted on a side surface of the slider block;
   a base;
   a revolving slide support comprising fluoroscopy radiological measurement indicia, wherein the slider block is slidably mounted on the revolving slide support, and the revolving slide support comprises a plurality of lock detents cooperating with a locking mechanism in the slider block to maintain position of the slider block; and
   a hinged mounting arrangement mounting the revolving slide support on the base.

* * * * *